(12) United States Patent
Adler

(10) Patent No.: US 8,025,314 B2
(45) Date of Patent: Sep. 27, 2011

(54) MEDICATION PACKAGING AND LABELING SYSTEM

(75) Inventor: Deborah Adler, New York, NY (US)

(73) Assignee: Target Brands, Inc., Minneapolis, MN (US)

( * ) Notice: Subject to any disclaimer, the term of this patent is extended or adjusted under 35 U.S.C. 154(b) by 1772 days.

(21) Appl. No.: 10/437,474

(22) Filed: May 14, 2003

(65) Prior Publication Data

US 2003/0214129 A1    Nov. 20, 2003

(51) Int. Cl.
| | |
|---|---|
| *B42D 15/00* | (2006.01) |
| *B65D 69/00* | (2006.01) |
| *B65D 71/00* | (2006.01) |
| *B65D 83/04* | (2006.01) |
| *B65D 85/42* | (2006.01) |
| *B65D 85/00* | (2006.01) |
| *G09F 3/00* | (2006.01) |

(52) U.S. Cl. .......... 283/81; 206/232; 206/534; 206/540; 206/459.5; 40/310; 283/900; 283/114

(58) Field of Classification Search .................. 220/662; 40/299, 310; 283/81, 66.1, 115, 900, 114; 206/530, 534, 459.5; 30/401, 120.011; D/7
See application file for complete search history.

(56) References Cited

U.S. PATENT DOCUMENTS

| | | | |
|---|---|---|---|
| D11,149 S | 4/1879 | Hood | |
| D18,997 S | 4/1889 | Underhill | |
| 406,017 A * | 6/1889 | Woodward | 40/310 |
| 605,213 A * | 6/1898 | Weller | 40/310 |
| 624,701 A | 5/1899 | Stevenson | |
| 716,793 A | 12/1902 | Vogeler | |
| D45,565 S | 4/1914 | Lloyd | |
| 1,181,098 A | 4/1916 | Lambert | |
| 1,223,933 A * | 4/1917 | Carr | 138/177 |
| 1,289,218 A | 12/1918 | Maiden | |
| 1,411,510 A | 4/1922 | Peterson | |
| 1,554,191 A | 9/1925 | Alexander | |
| 1,653,608 A | 12/1927 | Allen | |
| 1,686,354 A * | 10/1928 | Wallace | 40/310 |

(Continued)

FOREIGN PATENT DOCUMENTS

DE    3723671 C2    8/1988

(Continued)

OTHER PUBLICATIONS

English translation of JP10-297640A, 1998.*

(Continued)

*Primary Examiner* — Boyer D. Ashley
*Assistant Examiner* — Sara Addisu
(74) *Attorney, Agent, or Firm* — Griffiths & Seaton PLLC

(57) ABSTRACT

Method for generating a label for a medication in which information about the medication is obtained and printed on the label in a hierarchical manner with more important information in a more prominent location or more prominent type relative to other less important information. The information may be divided into primary information and secondary information with the primary information being placed on the label before the secondary information. The label may be used in a container having a curved front wall, a planar rear wall, a substantially planar bottom wall and a cap engaging with the front and rear walls to seal the container. The rear wall is constructed with a device for removably received an information card containing information relating to the medication.

7 Claims, 9 Drawing Sheets

U.S. PATENT DOCUMENTS

| | | | |
|---|---|---|---|
| 1,769,147 A | 7/1930 | Lennon | |
| 1,815,268 A | 7/1931 | Newbery | |
| 1,850,369 A * | 3/1932 | Andrews | 40/310 |
| 1,991,871 A * | 2/1935 | Sindler | 294/61 |
| 1,993,978 A * | 3/1935 | Plochman | 215/6 |
| 2,007,685 A | 7/1935 | Blake | |
| 2,110,768 A | 3/1938 | Kellogg | |
| D128,282 S | 7/1941 | Gelinas et al. | |
| 2,270,277 A | 1/1942 | Dowd | |
| D132,185 S | 4/1942 | McIntosh | |
| 2,328,806 A * | 9/1943 | Hoofer | 40/311 |
| 2,528,259 A | 10/1950 | Annunziata | |
| 2,659,614 A | 11/1953 | Cook et al. | |
| 2,717,463 A * | 9/1955 | Sindler | 40/324 |
| 2,847,971 A | 11/1956 | Painter | |
| 2,793,842 A * | 5/1957 | Bacon | 416/71 |
| 2,794,545 A * | 6/1957 | Olson | 206/217 |
| 2,844,893 A | 7/1958 | Keller | |
| 2,908,985 A * | 10/1959 | Hartman | 40/324 |
| 2,920,777 A | 1/1960 | Cole | |
| 2,961,108 A * | 11/1960 | Johnson | 215/228 |
| 2,995,265 A * | 8/1961 | Soderberg | 215/390 |
| 3,256,978 A | 6/1966 | Srigley et al. | |
| 3,298,671 A * | 1/1967 | Popma et al. | 206/223 |
| 3,331,521 A | 7/1967 | Paige | |
| 3,386,837 A * | 6/1968 | Arnot | 426/112 |
| 3,423,861 A * | 1/1969 | Forsyth | 40/662 |
| 3,433,378 A | 3/1969 | Ross | |
| 3,437,194 A | 4/1969 | Ames et al. | |
| 3,625,547 A | 12/1971 | Burke | |
| 3,628,266 A * | 12/1971 | Wise et al. | 40/654.01 |
| 3,757,994 A | 9/1973 | Skoetsch | |
| 3,772,809 A * | 11/1973 | Schneller | 40/637 |
| D230,137 S | 1/1974 | Bettonica | |
| 3,787,993 A | 1/1974 | Lyon | |
| 3,822,780 A * | 7/1974 | Ulmer et al. | 206/5.1 |
| 3,826,222 A | 7/1974 | Romick | |
| 3,850,326 A | 11/1974 | Ryles | |
| 3,923,180 A | 12/1975 | Fields | |
| 3,996,879 A | 12/1976 | Walton | |
| 4,022,352 A | 5/1977 | Pehr | |
| 4,044,889 A * | 8/1977 | Orentreich et al. | 206/459.5 |
| 4,061,783 A * | 12/1977 | Hoffman et al. | 426/87 |
| 4,064,645 A | 12/1977 | Wood | |
| RE29,793 E | 10/1978 | Pehr | |
| 4,143,786 A | 3/1979 | Goldberg et al. | |
| 4,150,760 A | 4/1979 | d'Orgelys | |
| D255,054 S * | 5/1980 | Kingsford | D28/89 |
| 4,246,709 A | 1/1981 | Selleslags | |
| 4,263,734 A | 4/1981 | Bradshaw | |
| 4,284,200 A | 8/1981 | Bush et al. | |
| 4,285,489 A * | 8/1981 | Blanchard | 248/471 |
| 4,334,638 A | 6/1982 | Stock | |
| D270,998 S | 10/1983 | Stark | |
| 4,428,384 A * | 1/1984 | Raitto | 600/573 |
| 4,483,622 A * | 11/1984 | Muhi et al. | 366/129 |
| 4,535,903 A | 8/1985 | Franchi | |
| D280,601 S | 9/1985 | Biesecker | |
| 4,550,602 A * | 11/1985 | Burke et al. | 73/428 |
| D282,909 S | 3/1986 | Biesecker | |
| D285,535 S | 9/1986 | Buchholz et al. | |
| 4,732,411 A | 3/1988 | Siegel | |
| 4,753,358 A * | 6/1988 | Virca et al. | 215/230 |
| 4,799,712 A | 1/1989 | Biava et al. | |
| 4,813,570 A | 3/1989 | Pontoppidan | |
| 4,819,351 A * | 4/1989 | Boitani | 40/654.01 |
| 4,860,899 A | 8/1989 | McKee | |
| 4,863,026 A * | 9/1989 | Perkowski | 206/232 |
| 4,868,027 A | 9/1989 | Hunkeler et al. | |
| 4,881,648 A | 11/1989 | Hagerty | |
| 4,883,180 A * | 11/1989 | Humphrey et al. | 206/534 |
| 4,890,742 A | 1/1990 | Allison | |
| 4,913,083 A | 4/1990 | Valvo et al. | |
| 4,918,604 A | 4/1990 | Baum | |
| 4,919,285 A | 4/1990 | Roof et al. | |
| 4,941,573 A * | 7/1990 | Fuerstman | 206/459.5 |
| 4,972,657 A | 11/1990 | McKee | |
| 4,991,877 A | 2/1991 | Lieberman | |
| 5,011,032 A * | 4/1991 | Rollman | 215/230 |
| 5,020,682 A | 6/1991 | Dutt | |
| D319,181 S | 8/1991 | Balavich | |
| 5,048,870 A | 9/1991 | Mangini et al. | |
| D324,994 S | 3/1992 | Jentgen | |
| 5,102,169 A * | 4/1992 | Mayfield | 283/115 |
| D328,246 S | 7/1992 | Nottingham et al. | |
| 5,145,080 A | 9/1992 | Imbery, Jr. | |
| 5,165,546 A | 11/1992 | Jaeger et al. | |
| 5,172,936 A | 12/1992 | Sullivan et al. | |
| 5,178,311 A | 1/1993 | McBride | |
| D333,618 S | 3/1993 | Patel et al. | |
| 5,193,032 A * | 3/1993 | Hirth | 359/804 |
| 5,204,775 A * | 4/1993 | McDevitt | 359/442 |
| 5,215,334 A | 6/1993 | Presson et al. | |
| 5,261,702 A | 11/1993 | Mayfield | |
| D342,452 S | 12/1993 | Monaghan | |
| 5,284,363 A | 2/1994 | Gartner et al. | |
| 5,301,802 A | 4/1994 | Nemeroff | |
| 5,309,279 A * | 5/1994 | Halstead | 359/442 |
| 5,342,093 A | 8/1994 | Weernink | |
| 5,343,647 A | 9/1994 | Bulka | |
| 5,346,069 A | 9/1994 | Intini | |
| D351,796 S | 10/1994 | Deddens | |
| 5,351,991 A | 10/1994 | McDonald | |
| D355,125 S | 2/1995 | Patel et al. | |
| D355,126 S * | 2/1995 | Paulovich et al. | D9/522 |
| 5,403,636 A | 4/1995 | Crum | |
| 5,448,844 A | 9/1995 | Miller, Jr. et al. | |
| 5,476,420 A | 12/1995 | Manning | |
| 5,495,944 A | 3/1996 | Lermer | |
| 5,588,239 A | 12/1996 | Anderson | |
| 5,601,314 A | 2/1997 | Burns et al. | |
| 5,642,906 A | 7/1997 | Foote et al. | |
| 5,660,138 A | 8/1997 | Hirsch | |
| 5,662,239 A | 9/1997 | Heuvelman | |
| 5,704,144 A | 1/1998 | Groth | |
| 5,704,648 A | 1/1998 | Brown et al. | |
| 5,713,681 A | 2/1998 | Venne et al. | |
| 5,718,347 A | 2/1998 | Walker et al. | |
| 5,719,828 A | 2/1998 | Haas et al. | |
| 5,729,922 A * | 3/1998 | Peterson et al. | 40/324 |
| 5,730,292 A | 3/1998 | Jones | |
| 5,758,440 A | 6/1998 | Yudin | |
| 5,760,975 A * | 6/1998 | DiGiovanni | 359/802 |
| D395,828 S | 7/1998 | Lecoule | |
| 5,779,072 A | 7/1998 | Krebs | |
| 5,788,974 A | 8/1998 | D'Amico et al. | |
| 5,799,815 A | 9/1998 | Lang | |
| 5,800,144 A | 9/1998 | Glenn et al. | |
| 5,829,789 A | 11/1998 | Treleaven et al. | |
| 5,887,736 A | 3/1999 | Mar | |
| 5,918,758 A | 7/1999 | Galton-Fenzi | |
| D413,067 S | 8/1999 | Haley | |
| 5,980,352 A * | 11/1999 | Rigberg | 446/73 |
| 6,003,902 A | 12/1999 | Petkovsek | |
| D419,077 S | 1/2000 | Sultan | |
| 6,023,865 A | 2/2000 | Preuss | |
| D423,361 S | 4/2000 | Negre | |
| 6,068,300 A | 5/2000 | Vijuk et al. | |
| 6,081,392 A * | 6/2000 | Pensmith | 359/802 |
| 6,086,702 A | 7/2000 | Rea | |
| D430,802 S | 9/2000 | Adachi et al. | |
| 6,127,013 A | 10/2000 | Todd | |
| 6,158,779 A | 12/2000 | Petrick | |
| 6,196,593 B1 | 3/2001 | Petrick et al. | |
| 6,209,921 B1 | 4/2001 | Hogan et al. | |
| 6,220,439 B1 * | 4/2001 | Virvo | 206/459.5 |
| 6,226,564 B1 | 5/2001 | Stuart | |
| 6,241,844 B1 | 6/2001 | Petkovsek | |
| 6,253,958 B1 * | 7/2001 | Coletti | 222/1 |
| 6,270,121 B1 * | 8/2001 | Dolan et al. | 283/81 |
| 6,276,725 B1 | 8/2001 | Laurash et al. | |
| 6,278,545 B1 * | 8/2001 | Napier | 359/440 |
| 6,360,462 B1 | 3/2002 | Mengel | |
| D456,271 S | 4/2002 | Maloney | |
| 6,366,401 B1 * | 4/2002 | Gonda et al. | 359/440 |
| 6,367,639 B1 | 4/2002 | Mar | |
| 6,367,640 B1 | 4/2002 | Julian | |

| | | | |
|---|---|---|---|
| 6,386,367 B1 * | 5/2002 | Bayliss, IV | 206/534 |
| D459,212 S | 6/2002 | Gobe | |
| 6,402,872 B1 | 6/2002 | Key | |
| 6,471,391 B1 * | 10/2002 | Opitz | 366/129 |
| 6,491,164 B1 | 12/2002 | Virvo | |
| 6,532,117 B2 * | 3/2003 | Taylor | 359/803 |
| 6,549,345 B1 * | 4/2003 | Cardarelli | 359/802 |
| 6,568,530 B2 | 5/2003 | Takahashi et al. | |
| 6,594,928 B1 | 7/2003 | Clawson et al. | |
| D480,002 S | 9/2003 | Canepa | |
| 6,621,629 B2 * | 9/2003 | Blumenthal et al. | 359/440 |
| D480,960 S | 10/2003 | Gray et al. | |
| 6,669,804 B2 | 12/2003 | Pendry et al. | |
| 6,681,945 B1 | 1/2004 | Harrold | |
| 6,712,398 B1 | 3/2004 | Fox et al. | |
| 6,722,495 B2 | 4/2004 | Fresnel | |
| 6,745,505 B2 * | 6/2004 | Moran | 40/311 |
| 6,752,272 B2 | 6/2004 | Jones et al. | |
| D497,311 S * | 10/2004 | Walsh et al. | D9/522 |
| 6,860,390 B2 * | 3/2005 | Bowman | 206/534 |
| 6,860,513 B2 | 3/2005 | Kaufman | |
| 6,964,345 B2 | 11/2005 | Wetherell, Jr. et al. | |
| D520,365 S | 5/2006 | Andoh | |
| D522,867 S | 6/2006 | Bakic | |
| D526,569 S | 8/2006 | Wurster et al. | |
| D539,651 S | 4/2007 | Snyder | |
| D540,179 S | 4/2007 | Adler | |
| D540,690 S | 4/2007 | Adler | |
| D541,159 S | 4/2007 | Robinson | |
| D542,661 S | 5/2007 | Adler et al. | |
| 7,225,937 B2 * | 6/2007 | Schroeder | 215/10 |
| 7,413,082 B2 * | 8/2008 | Adler et al. | 206/534 |
| 7,661,533 B2 * | 2/2010 | Adler et al. | 206/534 |
| 2001/0017817 A1 | 8/2001 | De La Huerga | |
| 2001/0054817 A1 | 12/2001 | Kelley et al. | |
| 2002/0020088 A1 | 2/2002 | Kreutner | |
| 2002/0041091 A1 * | 4/2002 | Eippert | 283/48.1 |
| 2002/0063739 A1 | 5/2002 | Gosden et al. | |
| 2002/0085290 A1 * | 7/2002 | Taylor | 359/803 |
| 2002/0088732 A1 | 7/2002 | Takahashi et al. | |
| 2002/0129758 A1 | 9/2002 | Hanley et al. | |
| 2002/0162261 A1 | 11/2002 | West et al. | |
| 2002/0171238 A1 | 11/2002 | Kozlowski et al. | |
| 2003/0025320 A1 | 2/2003 | Shoemaker | |
| 2003/0028392 A1 | 2/2003 | Davies | |
| 2003/0091687 A1 | 5/2003 | Copelan | |
| 2003/0127351 A1 | 7/2003 | Takahashi et al. | |
| 2003/0147450 A1 * | 8/2003 | Witonsky et al. | 374/141 |
| 2003/0192211 A1 | 10/2003 | Elias | |
| 2003/0193181 A1 | 10/2003 | Hung | |
| 2003/0193185 A1 | 10/2003 | Valley et al. | |
| 2003/0205897 A1 | 11/2003 | Kaufman | 283/117 |
| 2004/0045863 A1 | 3/2004 | Rhoades | |
| 2004/0050750 A1 | 3/2004 | Hannan et al. | |
| 2004/0056479 A1 | 3/2004 | Fox et al. | |
| 2004/0075272 A1 | 4/2004 | Kaufman | |
| 2004/0193454 A1 | 9/2004 | Foote et al. | |
| 2004/0232023 A1 | 11/2004 | Bansal et al. | |
| 2004/0237311 A1 * | 12/2004 | Brown et al. | 30/141 |
| 2005/0205513 A1 * | 9/2005 | Hidding | 215/246 |
| 2006/0016108 A1 * | 1/2006 | Watts | 40/299.01 |
| 2006/0163103 A1 | 7/2006 | Adler | |
| 2006/0163110 A1 | 7/2006 | Adler | |
| 2006/0163869 A1 | 7/2006 | Adler | |
| 2007/0029788 A1 | 2/2007 | Adler | |
| 2007/0102316 A1 | 5/2007 | Van Der Krogt et al. | |
| 2008/0264532 A1 * | 10/2008 | Wilson | 150/154 |
| 2009/0090688 A1 * | 4/2009 | Fruchter | 215/230 |
| 2010/0314351 A1 * | 12/2010 | Hoefling | 215/386 |

FOREIGN PATENT DOCUMENTS

| | | | |
|---|---|---|---|
| EP | 0 316 636 | | 5/1989 |
| EP | 0146095 B1 | | 8/1989 |
| EP | 0609955 B1 | | 4/1998 |
| EP | 0609954 B1 | | 7/1998 |
| EP | 0924676 A2 | | 6/1999 |
| FR | 2296391 A | * | 9/1976 |
| GB | 2 006 713 A | | 5/1979 |
| JP | 10297640 | | 11/1998 |
| JP | 10297640 A | * | 11/1998 |
| WO | 00/28474 | | 5/2000 |
| WO | 00/64676 | | 11/2000 |
| WO | 01/45028 A1 | | 6/2001 |
| WO | 03098275 | | 11/2003 |
| WO | 2004/048216 A1 | | 6/2004 |

OTHER PUBLICATIONS

"Multi-Dose, Multi-Color, I.V. Bag Rings," www.medidose.com/catalog/ivpharm/bagrings.htrnl, publicly advertised online at least as early as Apr. 27, 2002 based on the internet archive available at www.archive.org (1 page).
International Search Report, mailed Jan. 18, 2006, and Written Opinion, mailed Jul. 25, 2007, from International Patent Application No. PCT/US2005/019401.
U.S. Appl. No. 29/277,823, filed Mar. 9, 2007.
U.S. Appl. No. 29/277,825, filed Mar. 9, 2007.
U.S. Appl. No. 29/278,438, filed Mar. 29, 2007.
U.S. Appl. No. 29/278,568, filed Apr. 2, 2007.
European Search Report for Application No. EP03724594, dated Nov. 17, 2010.

* cited by examiner

FIG. 11

| SOPHIA LOWENSTEIN 360 W. 15 ST. APT. 5H 10003 | CVS/PHARMACY | RX# 45647885 (212)863-8873 |
|---|---|---|

PAXIL ● 20 MG

ANTI-ANXIETY

TAKE: 1 TABLET EVERY MORNING.

EXPIRES: JULY 10, 2003

REFILL: 03 QTY: 50 CAPSULES

DR. MILLER, VERONICA (631)555-6780
WRITTEN:07/10/03 DEA: BD50066970

SEE BACK FOR WARNINGS AND DRUG INFO

CAUTION: FEDERAL LAW PROHIBITS TRANSFER OF THIS DRUG TO ANY PERSON OTHER THAN FOR WHOM PRESCRIBED.

PAXIL (PAROXETINE)

INFORMATION YOU SHOULD KNOW BEFORE USING THIS MEDICINE

WHAT IS PAROXETINE?
PAROXETINE (pa-ROX-uh-teen) IS USED TO TREAT MENTAL DEPRESSION...

WITHOUT FIRST TALKING TO YOUR DOCTOR. IT MAY TAKE 4 WEEKS OR MORE FOR YOU TO START FEELING BETTER AND YOU MAY EXPERIENCE...

UNPLEASANT SIDE EFFECTS IF YOU STOP TAKING PAROXETINE SUDDENLY.

PRECAUTIONS:
TELL YOUR DOC...

MAY TAKE ESPECIALLY BARBITURATES, CIMITIDINE, ANTIDEPRESSANTS, MAO-INHIBITORS. IF YOU ARE UNSURE OF THE CONTENTS OR TYPES OF

MEDICATIONS YOU TAKE, ASK YOUR DOCTOR OR PHARMACIST. AVOID INTAKE OF ALCOHOL WHIHC CAN AGGRAVATE SIDE EF...

NOT KNOWN.

CHILDREN - NO SPECIFIC INFORMATION HAS BEEN TESTED ON CHILDREN.

...RING BABIES ARE

OLDER ADULTS - CONFUSION AND FALLING ARE MORE LIKELY TO OCCUR IN THE ELDERLY, WHO ARE MORE SENSITIVE THAN YOUNGER ADULTS

---

RECEIPT
OF
SALE
GOES
HERE

---

| SOPHIA LOWENSTEIN 360 W. 15 ST. APT. 5H 10003 | CVS/PHARMACY | RX# 45647885 (212)863-8873 |
|---|---|---|

PAXIL ● 20 MG

ANTI-ANXIETY

TAKE: 1 TABLET EVERY MORNING.

EXPIRES: JULY 10, 2003

REFILL: 03 QTY: 50 CAPSULES

DR. MILLER, VERONICA (631)555-6780
WRITTEN:07/10/03 DEA: BD50066970

SEE BACK FOR WARNINGS AND DRUG INFO

CAUTION: FEDERAL LAW PROHIBITS TRANSFER OF THIS DRUG TO ANY PERSON OTHER THAN FOR WHOM PRESCRIBED.

CVS/PHARMACY
230 E. 22ND ST. NY, NY 10546
(212)923-9200

PAXIL (PAROXETINE)

INFORMATION YOU SHOULD KNOW BEFORE USING THIS MEDICINE

WHAT IS PAROXETINE?
PAROXETINE (pa-ROX-uh-teen) IS USED TO TREAT MENTAL DEPRESSION...

WITHOUT FIRST TALKING TO YOUR DOCTOR. IT MAY TAKE 4 WEEKS OR MORE FOR YOU TO START FEELING...

UNPLEASANT SIDE EFFECTS IF YOU STOP TAKING PAROXETINE SUDDENLY.

PRECAUTIONS:
TELL YOUR DOC...

...ESPECIALLY BARBITURAES, CIMITIDINE, ANTIDEPRESSANTS, MAO-INHIBITORS. IF YOU ARE UNSURE OF THE CONTENTS OR TYPES OF

MEDICATIONS YOU TAKE, ASK YOUR DOCTOR OR PHARMACIST. AVOID INTAKE OF ALCOHOL WHIHC CAN AGGRAVATE SIDE EFFECT...
START OR...

...RING BABIES ARE

CHILDREN - NO SPECIFIC INFORMATION HAS BEEN TESTED ON CHILDREN.

OLDER ADULTS - CONFUSION AND FALLING ARE MORE LIKELY TO OCCUR IN THE ELDERLY, WHO ARE MORE SENSITIVE THAN YOUNGER ADULTS

MEDICATION PACKAGING AND LABELING SYSTEM

FIELD OF THE INVENTION

The present invention relates generally to an integrated medication packaging and labeling system and more specifically to a prescription medication packaging and labeling system which is designed to clearly provide information about the medication in order to avoid misuse of the medication.

The present invention also relates independently to a label for prescription medication, a method for generating a label for prescription medication, a container for prescription medication and an information card for prescription medication.

BACKGROUND OF THE INVENTION

Unfortunately, there are numerous instances in which prescription medication is misused with harmful and often fatal results. Misuse may involve a variety of different factors, such as taking the correct medication in an improper manner, at an incorrect time schedule and/or at an incorrect time with respect to meals, as well as taking the incorrect medication resulting from similarities between the shape, size, name and/or color of different medication and the bottles or containers in which different medications are dispensed.

Medication misuse often involves people, e.g., elderly people, who have difficulty reading and/or understanding the directions for using a particular medication. For example, it is known that Cardizem CD™, a prescription medication for blood pressure control, must be swallowed whole in order to be effective. This fact is indicated on the label that accompanies dispensation of the medication. However, elderly people may experience problems swallowing a large capsule and therefore might resort to breaking the capsule into smaller parts or chewing the capsule. This negates the pharmacological effects of the medication so that even though the patient is taking the medication, the desired control of the blood pressure is not being obtained in view of the misuse of the medication.

In the U.S., almost as much money is spent addressing the complications caused by home medication errors as is spent purchasing all the medications dispensed. Three years ago, almost $76 billion a year was spent purchasing medications in the U.S. while another $76 billion was spent treating medication errors including, but not limited to, errors caused by complications experienced by individuals as a result of misunderstandings in taking their medications. The cost of home medication increases ($180 billion+) when the costs to an employer for absenteeism, on-the-job injuries, etc. are included. Home medication errors are a national public health issue that is harming patients and the health care system, as well as the productivity of the U.S.

When a person is non-adherent, i.e., does not follow the proper instructions for taking medication, the cost of the treatment increases for both the consumer and the health care insurance provider. The wise use of prescription drugs can save lives. Prescription drugs should not be causing such high rates of medical complications and deaths as a result of people not being adequately informed. Home medication errors made by patients are linked to hundreds of thousands of deaths a year and cost this country nearly $180 billion in extra medical treatments.

In an attempt to avoid such misuse, accurate and detailed information is typically provided on labels affixed by a pharmacist to containers of prescription medication specifying the exact manner in which the prescription medication should be used.

Each pharmacy typically has its own label design that may be tailored to its specific needs as well as designed to be in compliance with any regulatory or statutory requirements. The label provides the prescription user with instructions and other necessary information to avoid misunderstandings that could lead to misuse of the medication. The information typically contained on the label includes the name, address and telephone number of the pharmacy, a prescription number, a date on which the prescription is prepared, an expiration date of the prescribed medication, the patient's name and address, the dosage and time schedule (e.g., 2 tablets every four hours), the prescribing doctor's name, the number of permissible refills, if any, the name of the medication, the number of capsules or tablets in the bottle, the weight of each capsule or tablet and indications as to whether the medication should be taken with meals, before meals, after meals, with liquids, not in combination with certain products, refrigerated, and the like.

There is no specific order in which the information provided on the label must be displayed. As such, each pharmacy's label is different. This causes inconveniences when one person has multiple prescriptions, each filled at a different pharmacy. Although the patient might be familiar with a label from one pharmacy and know where to look on that label to find information about taking the medication, he or she would have to search for the same information on a label from a different pharmacy.

In addition, when generating forms for prescription labels, pharmacies often do not prioritize the information, i.e., create an order in which the information is to be printed, for example, based on relevancy.

Thus, in a significant number of current prescription labels, there is no hierarchy of importance of the information contained thereon. Rather, it is often the case that the information about the pharmacy, including its logo, if any, is the most prominently displayed information.

Another inconvenience for patients taking medication relates to warning stickers which are applied to the containers at the pharmacy. Such warning stickers generally have a standard form and some warning stickers are bright orange or red with black printing. When placed on the containers, it is difficult to read the warnings since the black type does not stand out against the bright colors of the warning stickers, i.e., there is not sufficient contrast. Moreover, the red and orange warning stickers do not stand out against amber containers which are used in some pharmacies.

Another possible inconvenience arises when the stickers are affixed to the container and inadvertently cover up a significant amount of text on the label. This creates a problem for patients to read the information printed on the labels. In addition, the warning sticker also becomes difficult to read.

From the warning stickers to the placement of text on the labels to the size of the type used on the labels, there is no consistency in the labeling of prescriptions. As such, important information regarding the use of a medication is often overlooked since there is no indication that such information is important or even critical to the use of the medication. It would therefore be advantageous to provide a prescription labeling system in which information is placed in the order of importance so that important information is placed before information of lesser importance and is therefore not susceptible to being overlooked.

Another problem with prior medication systems is that the medication containers are usually cylindrical in shape such that the label is wrapped around the entire bottle. In this manner, the information printed on the label is difficult to read since, in order to read all of the information, the bottle must be held and rotated. It would be advantageous if all of the information about the prescription on a bottle were to be visible to a patient without having to rotate the bottle.

After dispensing the proper medication, most pharmacies place the filled container in a paper bag with printed information about the prescription as well as additional information about the prescription such as the price. The bag itself is typically branded with the pharmacy's identity and possible advertisements. The bag also may include information about the fastest way to refill the medication. The customer receipt and prescription information page are attached to the bag. The prescription information page is often a sheet of paper about 8.5 inches by 12 inches, folded, with text on both sides. The text is small and laid out with around 26 words per line. The prescription information page is thus often disregarded in view of the sheer amount of text thereon and the relatively small type. Such presents a problem as the information on the prescription information page is extremely important as it describes various properties of the particular drug such as what it is, how to use it, side effects, precautions, drug interactions, overdose, missed dose and storage. Sometimes, this is the only form of communication the patient has with the pharmacist.

OBJECTS AND SUMMARY OF THE INVENTION

It is an object of the present invention to provide a new and improved integrated medication packaging and labeling system and method.

It is another object of the present invention to provide a new and improved prescription medication packaging and labeling system and method which are designed to clearly provide information about the medication in order to avoid misuse of the medication.

It is yet another object of the present invention to provide a new and improved label for prescription medication that conveys information about the prescription in a clear and comprehensive manner.

It is another object of the present invention to provide a new and improved container for prescription medication.

Another object of the present invention is to provide a customizable packaging and labeling system for pharmacies and other prescription medication dispensing facilities which increases the confidence of the users of the system by enabling them to generate prescription labels with clearly structured information about the prescriptions utilizing both color and graphics.

To achieve these objects and others, a method for generating a label for a prescription medication for a patient in accordance with the invention comprises obtaining information about the prescription including the patient's name and home address, the name, form, purpose, dosage and expiration date of the medication, the manner in which the medication is to be taken, the number of refills of the prescription, the quantity of medication to be dispensed, the prescribing doctor's name and DEA number, and the date the prescription is written. The information is printed on the label in a hierarchical manner with more important information in a more prominent location or more prominent type relative to other lesser important information. An organized contrast is thereby provided between the different types of information with a view toward creating a clear and simple label that is easy to read and comprehend.

The information is divided into primary information and secondary information, i.e., information of lesser importance than the primary information. The primary information is placed on the label before the secondary information and would be information such as the patient's name and home address, the name, form, purpose and dosage of the medication and the manner in which the medication is to be taken. The secondary information is all other information. Arranging the information in this manner has been shown to increase patient comprehension when taking medication. For example, Dan Morrow, a psychology professor at the University of New Hampshire, has conducted a considerable amount of research in this area. See Daniel G. Morrow, Von O. Leirer, Jill M. Andrassy, Elizabeth Decker Tanke, and Elizabeth A. L. Stine-Morrow, "Medication Instruction Design: Younger and Adult Schemas for Taking Medication," Human Factors, 38 (1996): 556-573, which is incorporated herein by reference.

Instead of printing all of the information in a non-coherent manner on the label, the information which is printed on the label in accordance with the invention is placed in demarcated information areas, several such information areas being rectangular having an equal length and aligned with the left side of the label. Another information area may be vertically oriented alongside the rectangular information areas and is reserved for information about the dispenser of the medication, i.e., the pharmacy.

Additional features may be provided to facilitate easy identification of the medication. For example, the name of the medication is preferably placed in the largest font size and in black ink on a shaded background. Also, an icon or pictogram of the medication may be provided next to the name of the medication. This enables illiterate people to be able to identify their medicine by its form. In addition, the use of pictograms enables patients to detect mistakes in the dispensing of the medication, e.g., if the form of the medication does not correspond to the pictogram. The font, the font size and/or font type of the information in the information areas can be controlled and selected to increase the contrast of the information and highlight the more important information.

Color-coding is also used, e.g., by coloring one or more of the information areas, to convey information about the prescription. Such information might include the identity of a particular family member to whom the medication was prescribed (when each family member is assigned a separate color by the pharmacy) or the fact that the medication is high-risk. In addition, color-coding may be used to differentiate between different families of medications. For example, all heart medications can be colored pink.

A container for medication, to which the label described above may be affixed, is also provided in accordance with the invention. The container comprises a curved front wall, a planar rear wall, a substantially planar bottom wall and a cap engaging with the front and rear walls to close and seal the container. The label of the invention may be affixed to the front wall such that the information printed on the label is easier to read as compared to prior art medication bottles.

The rear wall of the container includes a device for removably retaining an information card that contains information relating to the medication. The retaining device may constitute a shoulder arranged at each lateral edge of the rear wall, each shoulder including an inwardly facing groove such that a slot receivable of the information card is defined by the grooves.

Thus, the system in accordance with the invention comprises a unique label, a unique medicine container and a unique information card. Together, these components serve as an interface that provides a reliable and safe alternative to current systems, which often fail to convey information in a clear and comprehensive manner.

BRIEF DESCRIPTION OF THE DRAWINGS

The invention, together with further objects and advantages thereof, may best be understood by reference to the following description taken in conjunction with the accompanying drawings wherein like reference numerals identify like elements.

FIG. 11 shows a sheet having a label section and data section created in accordance with the invention.

DETAILED DESCRIPTION OF THE INVENTION

Figure 1:
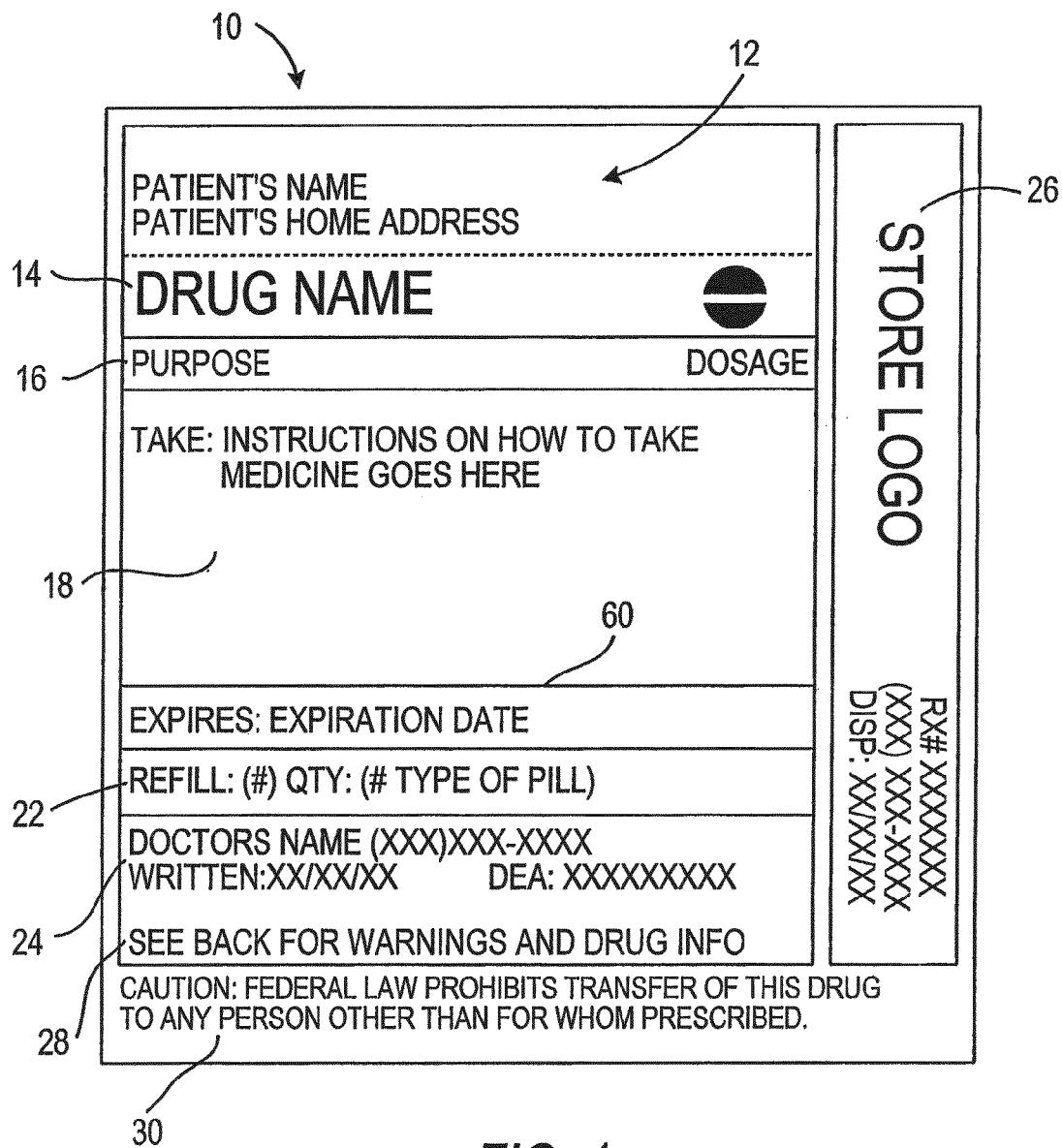
FIG. 1 shows a prescription label in accordance with the invention without information regarding a particular prescription.

Referring first to FIG. 1, a prescription label in accordance with the invention is designated generally as 10 and includes a unique arrangement of demarcated information areas in which specific information concerning the prescription is printed. The information to be printed in each information area is selected based in part on the importance of the information to the patient and with a view toward clearly conveying the proper use of the medication so as to avoid harmful and even potentially fatal errors in the use of the medication.

The arrangement and content of the label is designed to prevent the unfortunately all too common problem of people getting sick and sometimes dying due to mistakes such as misreading a dosage or not seeing a warning label when taking medication. Thus, the label is designed to make the medication user's experience less confusing. This is done by generally combing the ideas of information architecture with cognitive functions of older adults. The label is the result of a significant amount of research which determined the layout of instructional information.

Based on the research, an intuitive label is provided in which information to be presented thereon is divided into two categories, primary and secondary. The primary information reflects relatively important information, exactly what the patient wants and needs to know first to avoid misuse of the medication such as the name of the drug, its purpose, dosage and how to take it. The secondary information reflects information of lesser importance, such as the expiration date, quantity, name of the doctor prescribing the medication, how to reach the doctor, etc. The secondary information also includes the drug store, the refill number and the dispensing date. The hierarchy of the information, e.g., the order, position, type size, contrast, leading, alignment and choice of typefaces, is another important factor to a functional and clear label. In combination, the order of presentation of information and the manner in which the information is presented, coupled with the consumer's point of view, is crucial to the success of labeling system in accordance with the invention in the prevention of misuse of medication.

To achieve this purpose, the labels 10 are partitioned into a plurality of discrete information areas and a label dispensing machine can be used which prints the partitions lines when printing the information on the label. In the alternative, the labels can be pre-printed with the partition lines between the information areas. In general, the label 10 is formed on a substrate having an adhesive backing layer so that when the backing layer is removed, the label 10 can be affixed to a container via the adhesive layer.

A first information area 12 is arranged at the top of the label 10, extending almost entirely across the top of the label 10. Information area 12 is printed with the patient's full name and the patient's home address below the patient's name.

Information area 14 is arranged below information area 12 and is a shaded region in which the identification or name of the medication is printed. The identification of the medication may be the trademarked name of the medication, if this version is prescribed, or the equivalent generic name if a generic is available and prescribed or dispensed.

Information area 14 also includes an icon or pictogram 14a of the medication proximate the right edge of the information area 14. The presentation of the pictogram 14a serves to distinguish generally, for example, between capsules and tablets. By providing a pictogram 14a of the medication on the label 10, errors arising from taking the wrong medication can be prevented when two or more prescribed medications have different forms. For example, if a capsule is prescribed for one illness and a tablet for another, then the patient could view the pictogram 14a of the medication on the label 10 and know which medication is the right one to take. The patient would not have to consider even the name of the medication. Of course, this is not possible when the same type of medication is prescribed, such as two tablet-form medications.

In addition, the use of pictograms will enable patients to detect mistakes in the dispensing of the medication, e.g., if the form of the medication does not correspond to the pictogram. Possible pictograms 14a are discussed below with reference to FIG. 3.

Below information area 14 is information area 16 which contains a brief description of the purpose of the medication. A variety of purposes are designated for application by the label printing machine and may include "sleep-aid", "blood pressure control", "anti-biotic", "lowers cholesterol", "anti-histamine", "cough-cold", "migraine", "anti-anxiety", "anti-psoriasis" and "anti-arrhythmic". At the right edge of information area 16 is the dosage 16a of the medication, i.e., the strength or weight of the medication (10 mg, 20 mg, 100 mg, etc.).

A large information area 18 is arranged below information area 16 and includes the word "take" followed by instructions on the manner in which the medication should be taken. Precise and detailed instructions in plain language may be provided in view of the large size of information area 18. For example, possible instructions may be "1 to 2 tablets at bedtime as needed", "2 tablets before meals", "1 tablet every 12 hours", "swallow 2 tablets every six hours" and the like. The information area 18 can also include a notation of "HIGH ALERT" (as shown in the middle label 10 of the container shown in FIG. 7) or a warning not to take more than a specific number of capsules or tablets per day.

The information in information areas 12, 14, 16, 18 may be considered the primary information in that it is the basic information needed to properly administer or take the medication. The name of the patient for which the medication is prescribed is necessary to avoid the situation where one person takes another medication. The name of the medication is necessary to avoid the situation where the wrong medication is taken. The purpose of the medication is necessary to clarify the condition and reason why the medication is being taken so that if the condition is no longer present, the medication would not be required. This happens when a medication is taken as a pain reliever so that once the pain is no longer present, the medication can be stopped. The instructions about how to take the medication are necessary to avoid the situation where the medication is taken improperly and thus may not provide its intended and expected benefits.

Additional information is also printed on the label 10 and is considered the secondary information in that it is less important for correct usage of the medication than the primary information. To this end, information area 20 is arranged below information area 18 and includes information about the expiration date of the medication, the date beyond which the medication may not be effective. Information area 22 is below information area 20 and includes information about the number of possible refills of the medication and the quantity of tablets or capsules in the prescription. The label 10 includes the word "expires:" following by space for the expiration date, the word "refill:" following by a space for number indicative of the number of refills available, and the word "qty:" or "quantity" following by a space for the quantity of tablets or capsules in the prescription.

Information area 24 is below information area 22 and includes information about the doctor prescribing the medication, including for example, his or her phone number and optionally the address, the date the prescription is written and the doctor's DEA number.

Information areas 12-24 are substantially rectangular and have a common length. The width of the information areas 12-24 varies as shown in FIG. 1. The demarcation lines between the various information areas are usually 0.5 in weight and 30% black. However, the line 60 between the primary information in information area 18 and the secondary information in information area 20 is twice as thick and 1 pt in weight and 100% block. This demarcation line separates the primary information from the secondary information.

Another information area 26 is arranged at the right of information areas 12-24 and the print therein is vertically oriented. Information area 26 includes the logo of the store or pharmacy dispensing the prescription and information about the store or pharmacy including for example, the prescription number, the phone number and optionally the address, and the date the prescription is dispensed.

To complete the label 10, other printed information can also be provided if desired, needed and/or required by law. For example, as shown in FIG. 1, the label 10 includes an indication that warnings and drug information is on the back of the label (information area 28) and a cautionary statement that federal law prohibits transfer of the drug to any person other than the patient for whom the drug is prescribed (information area 30). The indication in information area 28 is black print on a color background and the particular color used is indicative of the type of warning. This feature is discussed in greater detail below.

In addition to the arrangement and content of the information areas 12-26, the font, type and capitalization used to print the information is selected to optimize the conveyance of information about the prescription and its usage. Specifically, the printed information has different types with more important information printed in a larger type than information of lesser importance. As an example, in the label illustrated in FIG. 2, the name of the medication in information area 14 has the largest font (15.5 pt) and is printed in capital letters in view of its overriding importance. The patient's name in information area 12 has the next largest font (12 pt) following by the instructions in information area 18 in 11 pt (the word "take" in information area 18 being slightly smaller in 10 pt) and the information in information areas 20 and 22, i.e., the expiration date, refill number and quantity, also in 11 pt (the words "expires:", "refill:" and "qty:" being slightly smaller in 10 pt). The purpose of the medication in information area 16 is printed in 9.5 pt and the patient's address in information area 12 and the doctor's information in information area 24 is printed in 8.5 pt. In information area 26, the prescription number, and the phone number are printed in 8.5 pt while the date the prescription is dispensed is printed in 7.5 pt. The dosage information printed in information area 16 is printed in 8 pt. The indication in information area 28 is printed in 8 pt and the federal warning in information area 30 is printed in 7 pt.

With respect to the font, it has been found that the Myriad Roman font is an extremely advantageous font since it provides clear letters when used either plain, in an italics mode or in a bold or semi-bold mode. The particular mode of the Myriad Roman font used for the information printed in each information area is preferably selected to optimize the conveyance of information on the label. (In the label illustrated in FIG. 2, only the federal warning in information area 30 has a different font, i.e., Helvetica condensed.)

Figure 2:
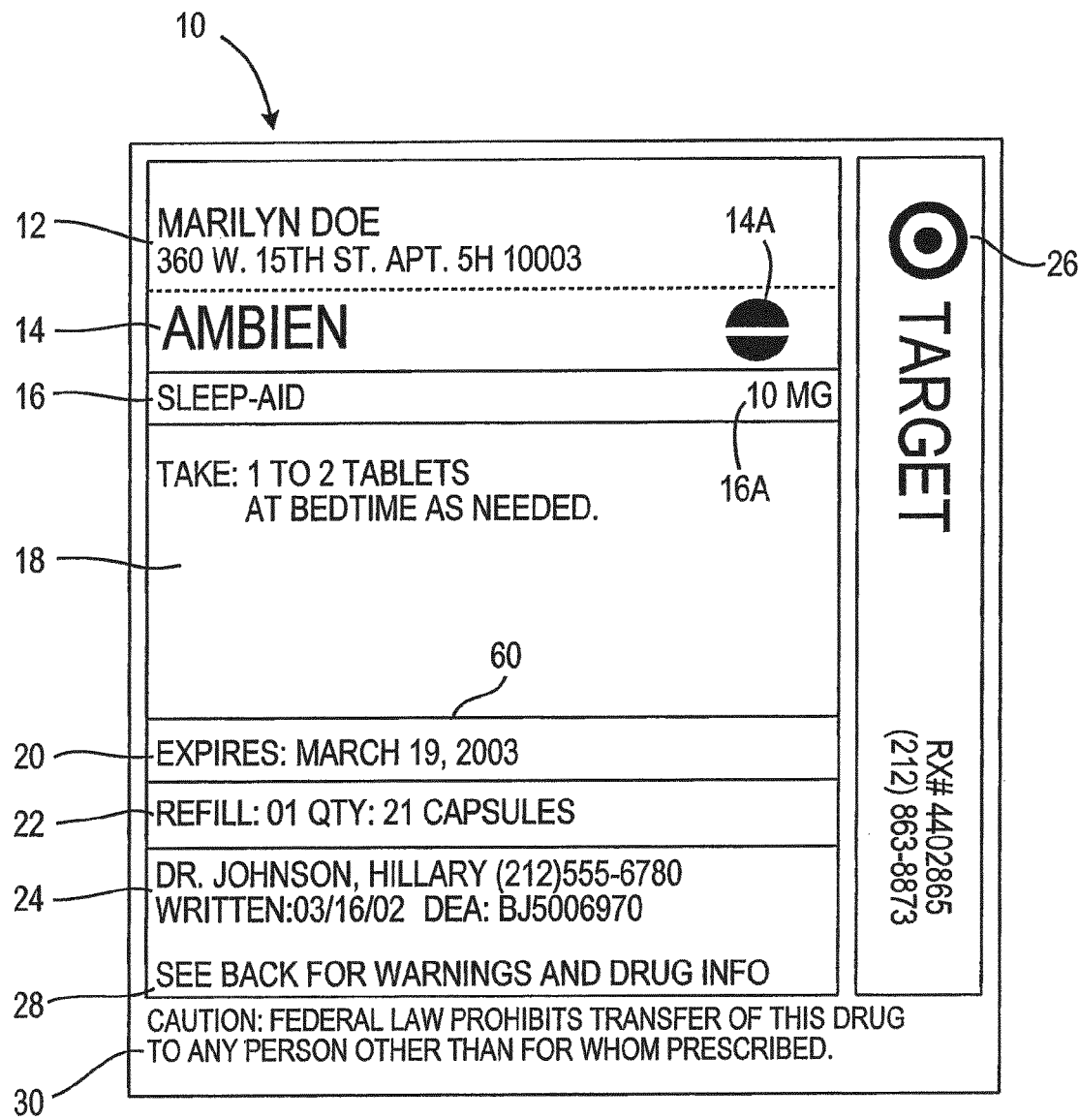
FIG. 2 shows a prescription label in accordance with the invention including information about a prescription.

In the embodiment illustrated in FIG. 2, the patient's name is printed in italics and the name of the medication, the patient's address and the doctor's name and DEA information are printed in capitals. Bold print is used for the name of the medication in information area 14 and the phone number of the pharmacy and the prescription number in information area 26. A semi-bold print is used for the purpose of the medication in information area 16, the doctor's name and the notation "DEA:" in information area 24 and the expiration date, refill number and quantity in information area 20. Small caps are used for the indication in information area 28.

In addition, the numbers relating to the instructions for taking the medication, in information area 18, may also be printed in bold type. This will serve to highlight, for example, the number of tablets and/or the hours between taking the medication. An instruction can therefore be, for example, "1 or 2 capsules every 4 hours as needed". This clearly conveys to the patient the proper administration of the medication.

As also shown in FIG. 2, all of the text (except the dosage in information area 16 and the pharmacy information in information area 26), should preferably be left-justified and lined up.

As noted above, the indication in information area 28 is printed in black ink on a color background. It is possible to obtain numerous different colors using any commercially available color printer which can be adapted to print prescription labels. Possible colors used in the invention are green, orange, blue, gray, pink and yellow and these colors, as well as possibly other colors, can easily be produced by most any color printer.

The color of the information area 28 can be used to convey specific information designed to prevent misuse of the medication. For example, each member of a family can be assigned a different color and whenever that member has a prescription filled, the information area 28 will be printed in that color. In this manner, each member will know only to take medication having his or her color. This will enable each patient to take the correct medication in a situation where two members of the same family are taking the same medication but different doses, e.g., one is taking Ambien 10 mg and the other is taking Ambien 50 mg. By color-coding at least a portion of the label, and associating each individual color with a particular family, member, each family member will know only to take medication having his or her assigned color thereon.

Assignment of different colors to different family members may be done when the family first fills a prescription at a pharmacy incorporating the labeling system in accordance with the invention. The family member would complete a form listing the family members and each would select or be assigned a color for the label. The system would prevent the selection or assignment of the same color to more than one family member. If a patient-consumer lives alone, he or she can always choose a default color. Instead of assigning different colors to different family members, it is also possible to use color-coding for morning pills and nighttime pills. This might be used by a person living alone. As such, he or she could code labels pertaining to morning pills one color and their evening pills another color. Alternatively, color-coding can be used universally to differentiate between different families of medications.

The use of a particular color on the label is a quick and easy way for a patient to identify a particular medication since color is mentally processed in a short amount of time. Use of color therefore helps avoid confusion when multiple medications are present. Instead of limiting the color-coded portion to information area 28, other portions of the labels can be colored, for example, the borders or possibly information area 14.

In some instances, it might be desirable to use a specific color, such as red, on a portion of the label to identify high-risk medications.

Figure 3:
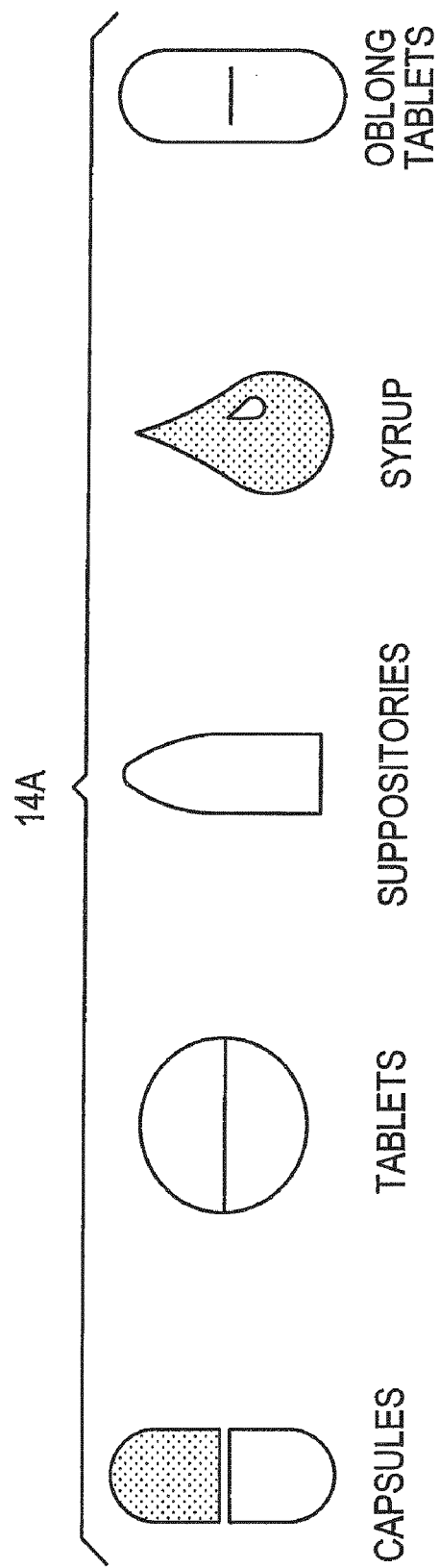
FIG. 3 shows various pictograms used on a label in accordance with the invention.
Figure 6:
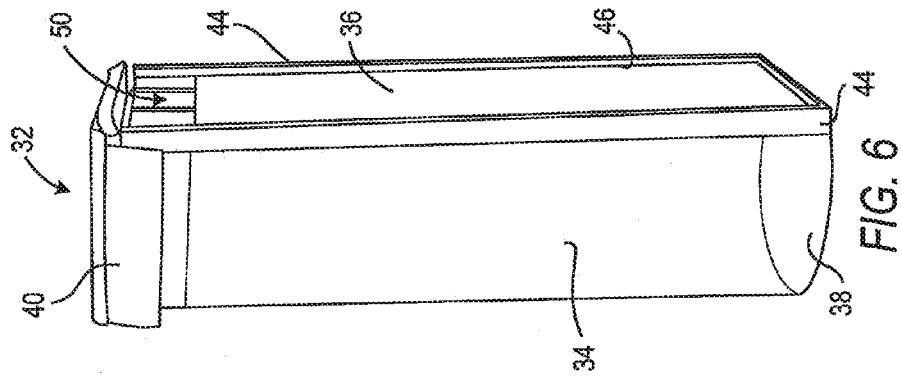
FIG. 6 is a side view of the container shown in FIG. 5.
Figure 5:
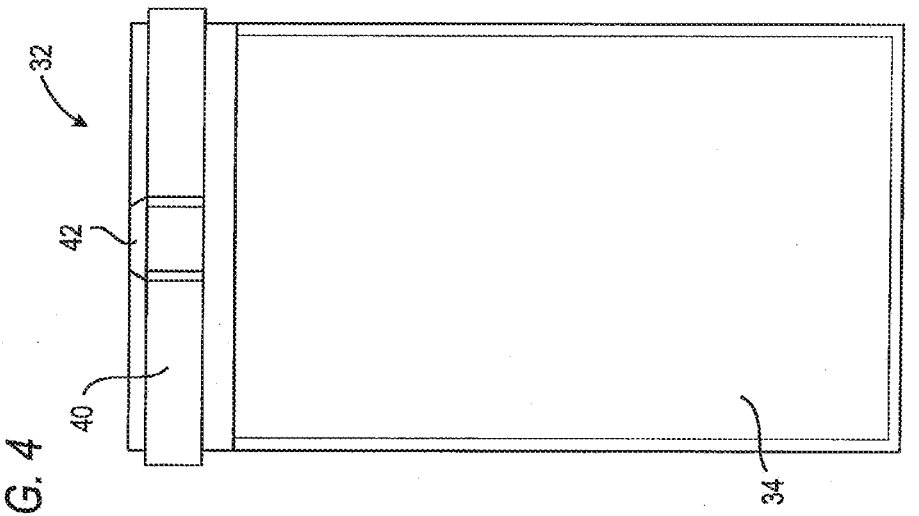
FIG. 5 is a front view of a container in accordance with the invention to which the label shown in FIG. 1 can be applied.

FIG. 3 shows possible icons or pictograms 14a of medications which can be printed in information area 16 alongside the name of the medication. The pictograms 14a include one for capsules which is oval and divided in half with each half being colored differently, one for tablets which is round and divided in half, one for suppositories having the general shape of a suppository, one for syrup having the shape of a drop of fluid and one for oblong tablets which is oval with a line in the middle and uncolored.

As noted above, by displaying a pictogram of the medication on the label, when multiple medications are prescribed having different forms, the pictogram provides a quick and easy way to determine the medication (assuming it is known that one medication is in one form and the other medication is in another form). In addition, displaying a pictogram of the medication on the label allows the patient to detect if the medicine in the container to which the label 10 is affixed does not match the pictogram 14a. If so, the patient will hopefully avoid taking the medication and clarify the situation as to which medication should be taken.

Figure 4:
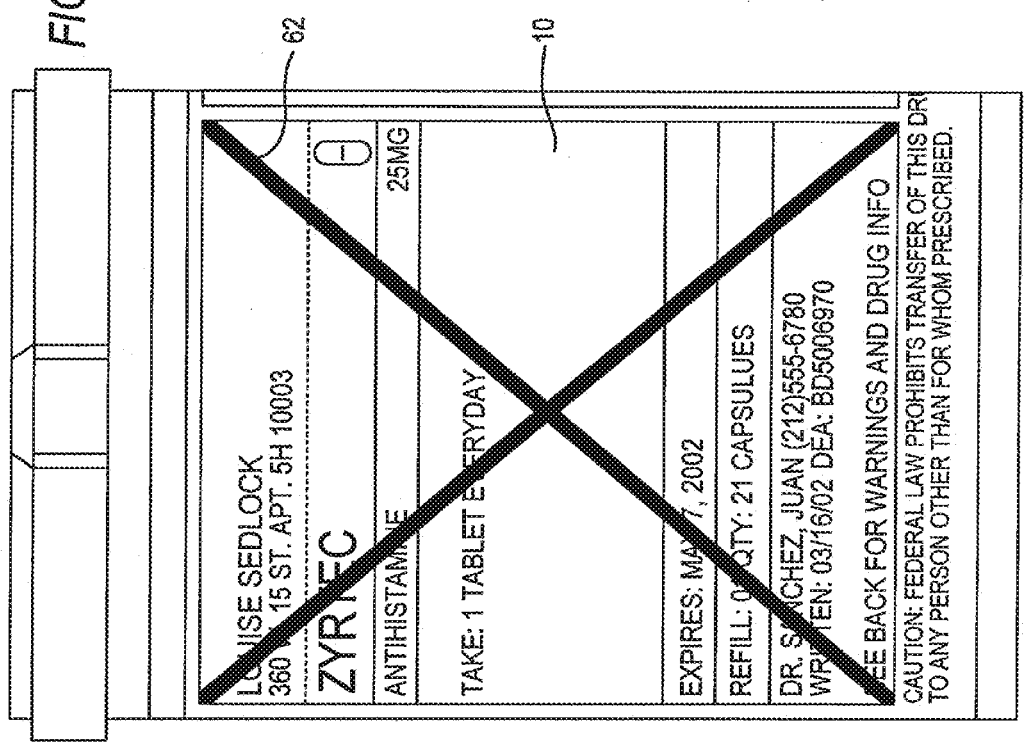
FIG. 4 shows an embodiment of the invention with a self-expiration feature.

Referring now to FIG. 4, the label 10 in accordance with the invention can be provided with a self-expiration mark 62. This type of mark 62 is useful because many medications lose their potency over time and become unsafe if used beyond the expiration date.

The label 10, when generated, is provided with a time-released expiration mark 62, such as stripes of red color against a white background, which appear on the label 10 when the medication has expired. While initially the label 10 has a generally white background, stripes of color will appear upon expiration of the medication notifying the user that the medication has expired. If the label has a big red "X" going through it, it should be clear to the patient that the medicine is no longer effective and could be dangerous.

The application of a time-release expiration mark to labels has been developed by Temtec Inc. of Suffern, N.Y. which makes a product called TempBadge. The following U.S. patents owned by Temtec are incorporated herein by reference: U.S. Pat. Nos. 4,605,246, 5,446,705, 5,602,804, 5,633,835, 5,640,742, 5,699,326, 5,715,215, 5,719,828, 5,755,175, 5,785,354, 5,822,280, 5,862,101, 5,873,606, 5,930,206, 5,947,369, 5,957,458, 6,086,971, 6,197,396 and 6,295,252.

Referring now to FIGS. 5-8, the label 10 described above can be applied to any conventional containers or can be used in combination with a specially designed container designated generally as 32. Container 32 has a curved, preferably semi-circular, vertically oriented front wall 34, a planar rear wall 36, and a substantially planar bottom wall 38 having an edge that conforms to the curvature of the front wall 34. A cover or cap 40 engages with the front and rear walls 34,36 at an upper portion thereof to close the container 32. Cap 40 includes a tongue portion 42 to facilitate opening of the cap 38 and access to the medication in the container 32.

The container 32 in accordance with the invention thus does not have the conventional cylindrical form. Several advantages are provided by the container 32 in accordance with invention. The user should feel comfortable using the container 32 since it is similar to the existing cylindrical containers, and not entirely different as would be the case if a container having a rectangular cross-section were to be used.

It has also been found that it is easier to read information on a semi-circle as opposed to having information printed all around a cylindrical container which would require the container to be turned in a complete circle to obtain all of the information printed thereon. Turning the container creates fragmented instructions.

In addition, the rear of the container 32 is planar and includes a retaining device which enables an information card and/or magnifying lens to be retained in a fixed position relative to the container. The information card would thus be easy to read without requiring any turning of the container 32.

Moreover, the semi-circular shape of the container 32 takes up less space in medicine cabinets and on kitchen counters where medication is usually stored.

The rear wall 36 of the container 32 includes at least one retaining device for enabling an information card 48 or magnifying lens to be retained in a fixed position relative to the container. A shoulder 44 is formed along each lateral edge of the rear wall 36 extending from the bottom of the rear wall 36 to the top of the rear wall 36 and each shoulder 44 includes a groove or ridge 46. An information card 48 (discussed below) or any other relevant material can slide in and out of a slot 50 formed by the grooves 46. Instead of opposed grooves 46 for holding the information card 48, other constructions, such as a pocket, could also be provided. It is also possible to attach the card directly to the rear wall of the container using a magnet or Velcro arrangement. The slot 50 may be dimensioned to accommodate any size of paper.

The slot 50 formed by the grooves 46 can be used by pharmacists to display special notes on the information card 48 for the patient. The note would be printed on the information card upon printing of the label 10. For example, the time the patient should take their medication can be printed on the card 48. The card 48 can also include warnings regarding the medication.

Figure 9:
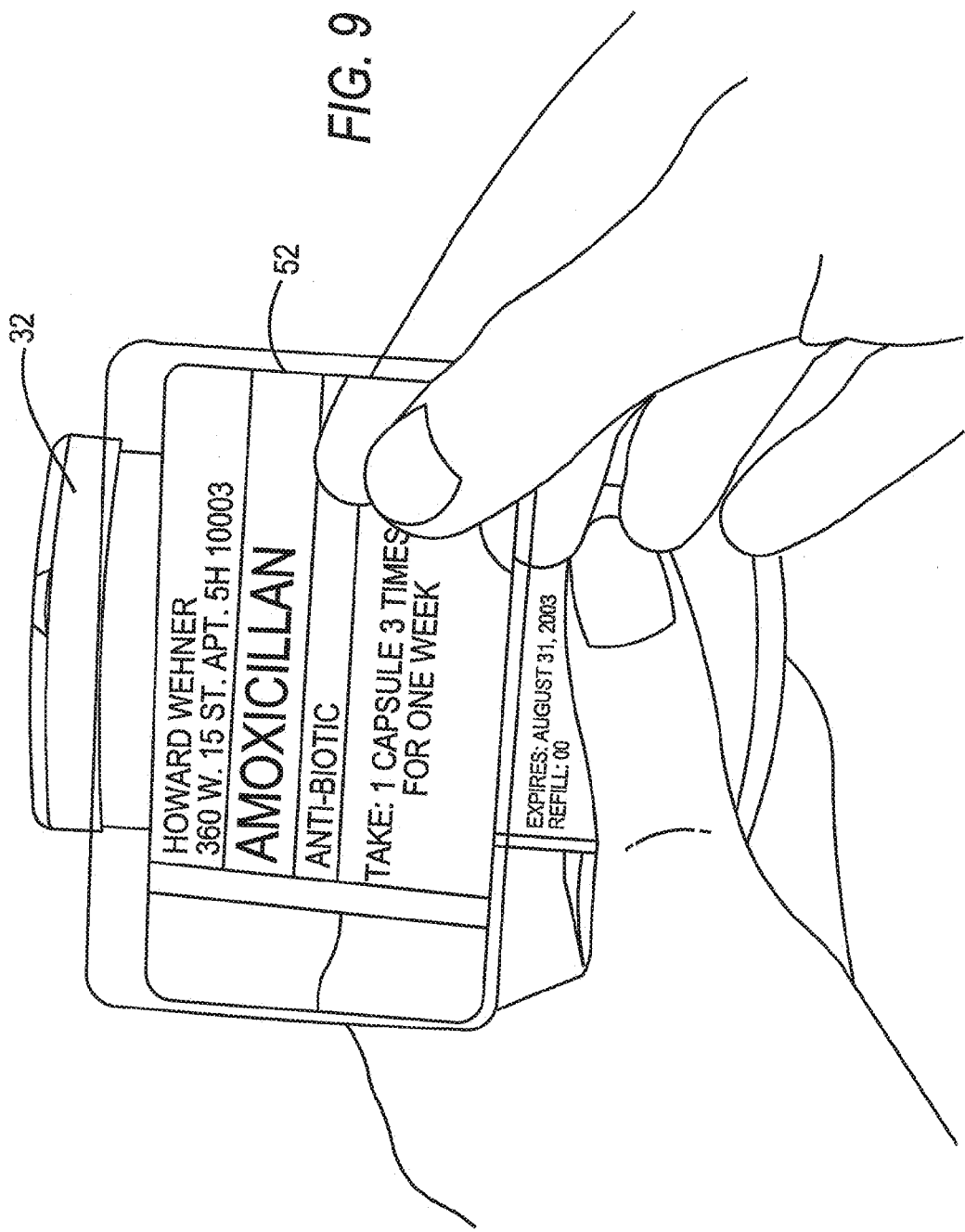
FIG. 9 shows the magnifying lens which can be placed in connection with the container in accordance with the invention.

The slot 50 can also be used to hold a magnifying lens 52 which magnifies the medication in the container 32 to make it more clearly visible to the patient (see FIG. 9). The magnifying lens 52 would be beneficial to include with the container 32 for visually impaired and elderly patients or for patients who are frustrated by small typefaces.

In the preferred embodiment of the invention, the information card 48 is not affixed to the container 32 but rather is removably received in the slot 50. This is possible because the information card 48 would typically contain information supplemental to that on the label 10 so that as long as the label 10 is still affixed to the container 32, the medication can be properly taken. However, when the information card is not affixed to the container, warning stickers appearing on the back of the information card are also affixed to the planar surface of the container so that, if the card is removed, the warning stickers remain visible to the patient.

In another embodiment of the invention, the information card 48 is affixed to the container. In this embodiment, the card 48 is affixed at one of its edges and the card is folded so that it rests flush with the planar edge of the container. The patient unfolds the card 48 in order to read its contents.

The containers 32 may be constructed in various sizes. Medication containers are measured in drams and the number of drams reflects the content size of the bottle. At least three different size containers 32 are envisioned, namely, a large size (90 dram, about 4 inches by 2.75 inches), a medium size (30 dram, about 3.75 inches by 2 inches) and a small size (10 dram, about 3 inches by 1.75 inches). The size of the container 32 used by the pharmacist is selected according to the amount of medication prescribed.

In view of the different sizes of containers 32, the label 10 is also provided with different sizes, one to fit each of the different containers.

To produce the containers 32, an initial prototype mold of the container is made. The initial mold has a single cavity into which plastic is injected. A cavity is the space that forms the product by having plastic injected into it. A container designer works with the prototype until it meets with approval. Once a perfected prototype is complete, a multi-cavity mold can be made. The price of the mold varies according to the size of the container and how many cavities there are. Once a mold is approved, production of the containers can proceed. The containers 30 may be made of inexpensive recyclable plastic purchased from any number of suppliers. A common type is polypropylene.

Figure 8:
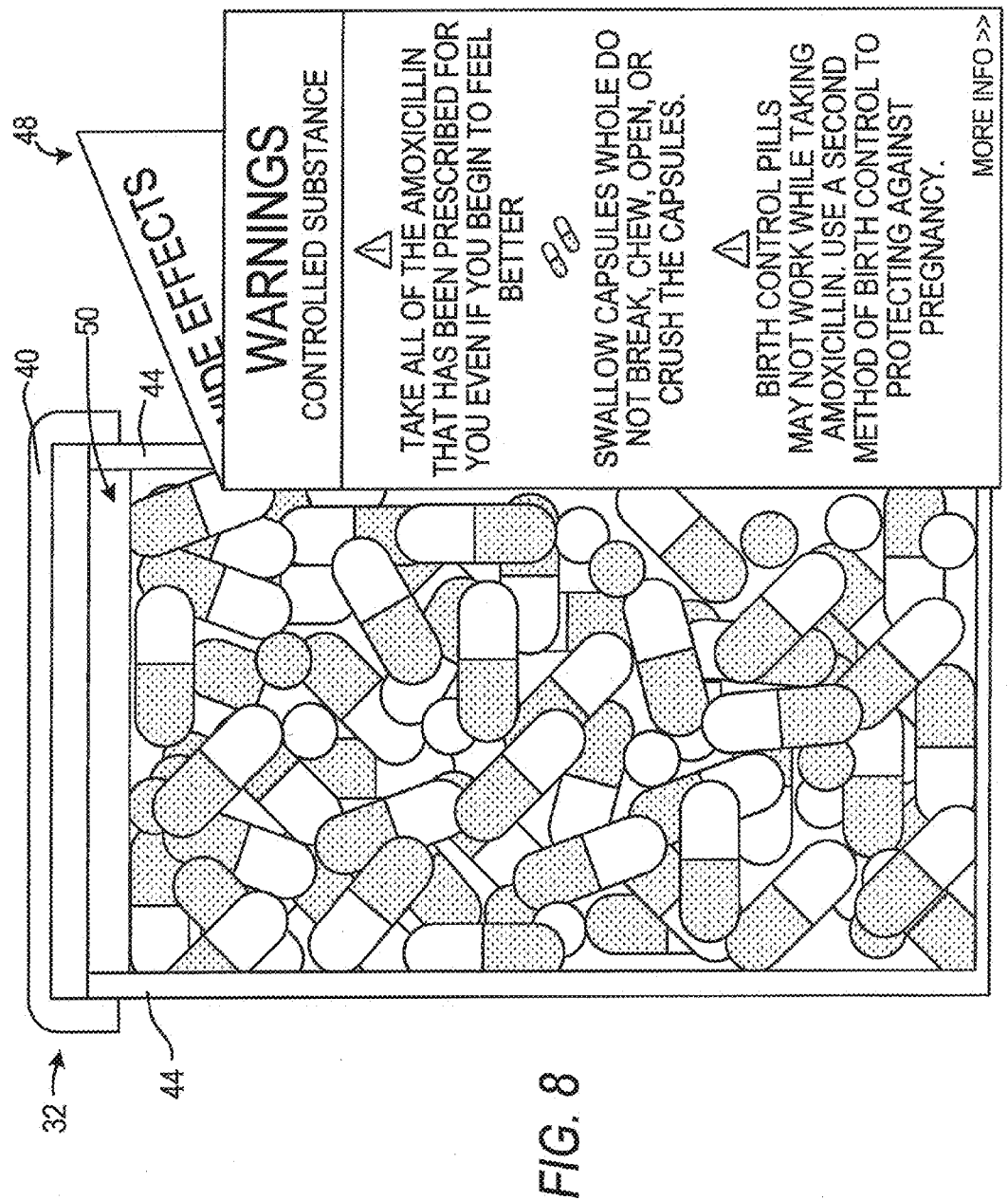
FIG. 8 shows an information card in accordance with the invention alongside a container in accordance with the invention.

Another novel feature of the invention is the particular construction and content of the information card 48 (see FIG. 8). The information card 48 is usable independent of the label 10 and the container 10, although preferably, the label 10, the container 32 and information card 48 are used in combination with one another to provide optimal protection against misuse of the prescribed medication.

In contrast to the prior art practice of providing information regarding the prescribed medication printed on sheets of paper with long lines of small type, the information card 48 in accordance with the invention is an easy-to-read, fold-out card that fits into the slot 50 formed by the grooves 46 on the rear wall 36 of the container 32. In view of the different sizes of containers 32, the card 48 will also be fabricated in three different sizes, one to fit each container 32. The card 48 thus has a width of approximately twice the width of the slot 50 so that when folded in the middle, it will be securely retained in the slot 50. The card can also be folded more than two times in which case, its width will be equal to the width of the slot 50 times the number of folded sections.

The information card 48 serves several purposes. The card provides the patient with warnings and side effects about the medication. When a patient opens the card, he or she can read information and facts about the particular drug. The warnings are placed on top of one another facing outward and thus are the first thing the patient sees when he or she turns the container 32 around. Even if the patient does not remove the information card 48 from the slot 50, he or she will be able to see the warnings. These warnings are designed to replace the current warning stickers.

Figure 7:
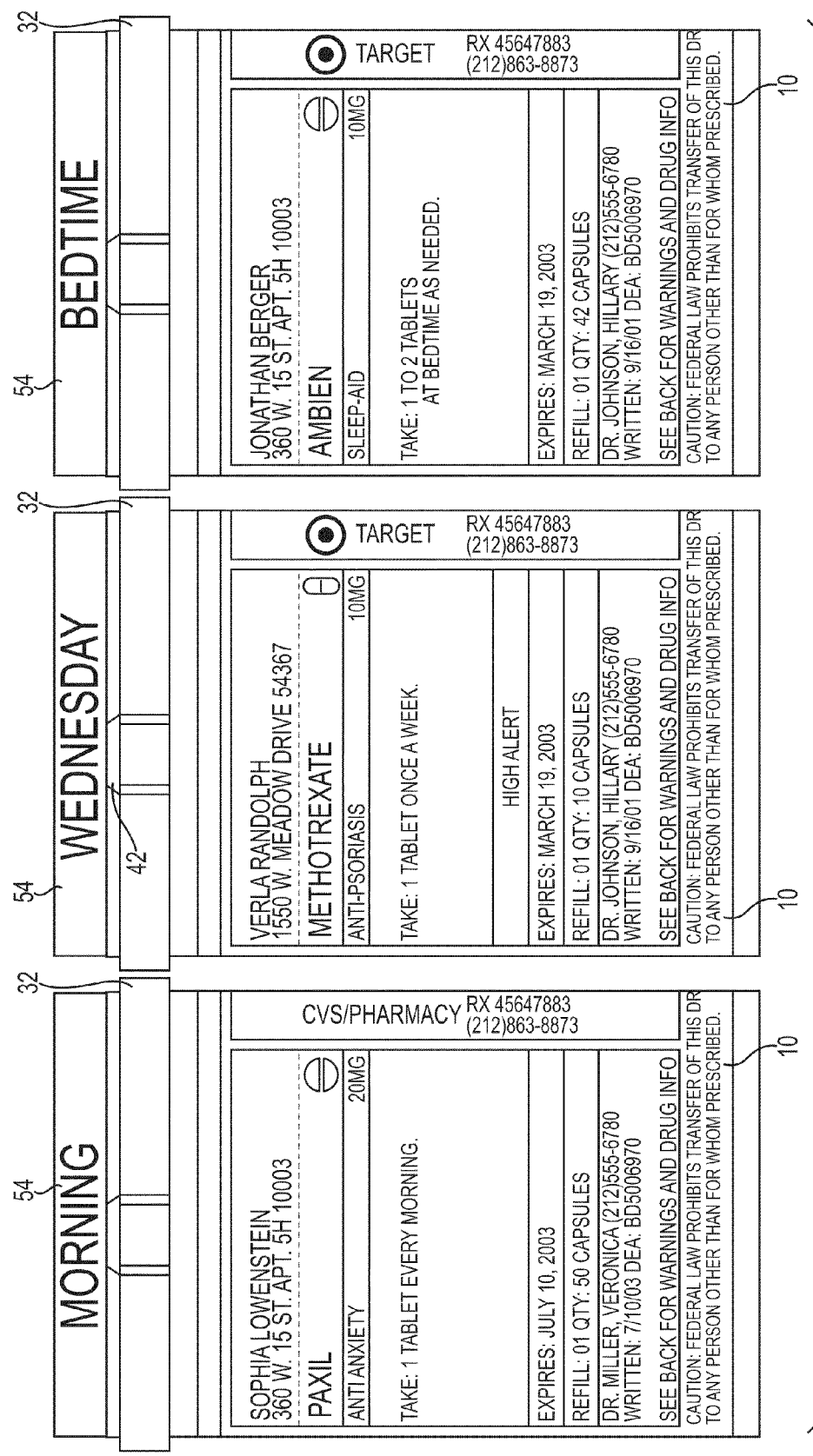
FIG. 7 shows several containers in accordance with the invention having labels in accordance with the invention applied thereto.

The information card 48 also provides a space for pharmacists to enter additional notes that will help the patient comply with, e.g., dosage instructions. As shown in FIG. 7, the information card 48 is retained in a fixed position relative to the container such that a portion 54 at the upper edge of the information card 48 extends beyond the cap 40 on which a pharmacist or doctor may enter notes such as the time of day the medication should be taken ("BEDTIME", "MORNING", etc.). The information card 48 can then be positioned such that the portion 54 is visible when the container 32 is stored, e.g., in a medicine cabinet.

An additional card can be stapled to the bag in which the prescription is delivered and/or sold. This copy may be kept in the patient's wallet in case of an emergency. Since the card is easily accessible, it can be used as a reference whenever necessary.

The information card 48 may be made formed of a waterproof material or sealed to be waterproof so it can be stored in a bathroom without risk of getting wet. Ideally, a patient collects an additional copy of each card and, by reviewing the card, is readily able to ascertain what medications he or she is taking.

The information card 48 can be used with containers having different shapes than container 32. For example, information card 48 can be used in connection with any container having a flat side, such as a rectangular or square container. The information card 48 can also be used for cylindrical containers in which case, shoulders 44 can be formed at two peripheral locations around the container and the information card would be bent around a portion of the circumference of the container. Thus, the information card 48 can be used independent of the label 10 and container 32 described above.

Accordingly, a comprehensive labeling and packaging system for prescription medication is provided in accordance with the invention which seeks to benefit consumers by delivering instructions, warnings and knowledge about medications in a clear and simple manner in order to avoid the incorrect use of medication. By creating a clear, well thought-out system for labeling and packaging medications, an improved dispensing system will be created which will provide benefits to all parties involved. The medical industry will experience a decrease in medical errors, health insurance companies will profit as a result of lower hospital bills, drug companies will face fewer lawsuits, pharmacists and doctors will be able to identify different drugs and dosages and consumer's experience with the health care industry will be more satisfying As to consumers, the system in accordance with the invention will likely provide the greatest benefit to prescription users over the age of 65. This group is at the highest risk of medication errors. There are currently more than 35 million Americans over the age of 65, and approximately 6.3 million may not be able to correctly read the directions that appear on their medicine labels. This problem is only going to worsen as the baby boomer generation grows older.

The system in accordance with the invention is designed to be easily readable for people 65 and older. In view of the presence of pictograms and the use of bold, clear typeface, among other features, illiterate and non-English-speaking citizens can also benefit from the invention. There are currently 40 million Americans who are functionally illiterate (reading at or below a fifth-grade level). Yet, like everyone, they need to understand how many times a day they should take their medication and what the side effects are.

Consumers will also benefit by the presence of distinguishing marks on the label that may alert the pharmacist of the need to provide particular, important information. For example, most pharmacists use automatic label printing machines which generate labels. In accordance with the invention, labels for some medications would be generated with marking indicating a "HIGH ALERT" (in information area 18) or a particular color in a specific region (the color red in information area 28). Upon seeing one of these markings, the pharmacist is informed of the need to explain information about the product to the patient to avoid possible misuse.

Figure 10:
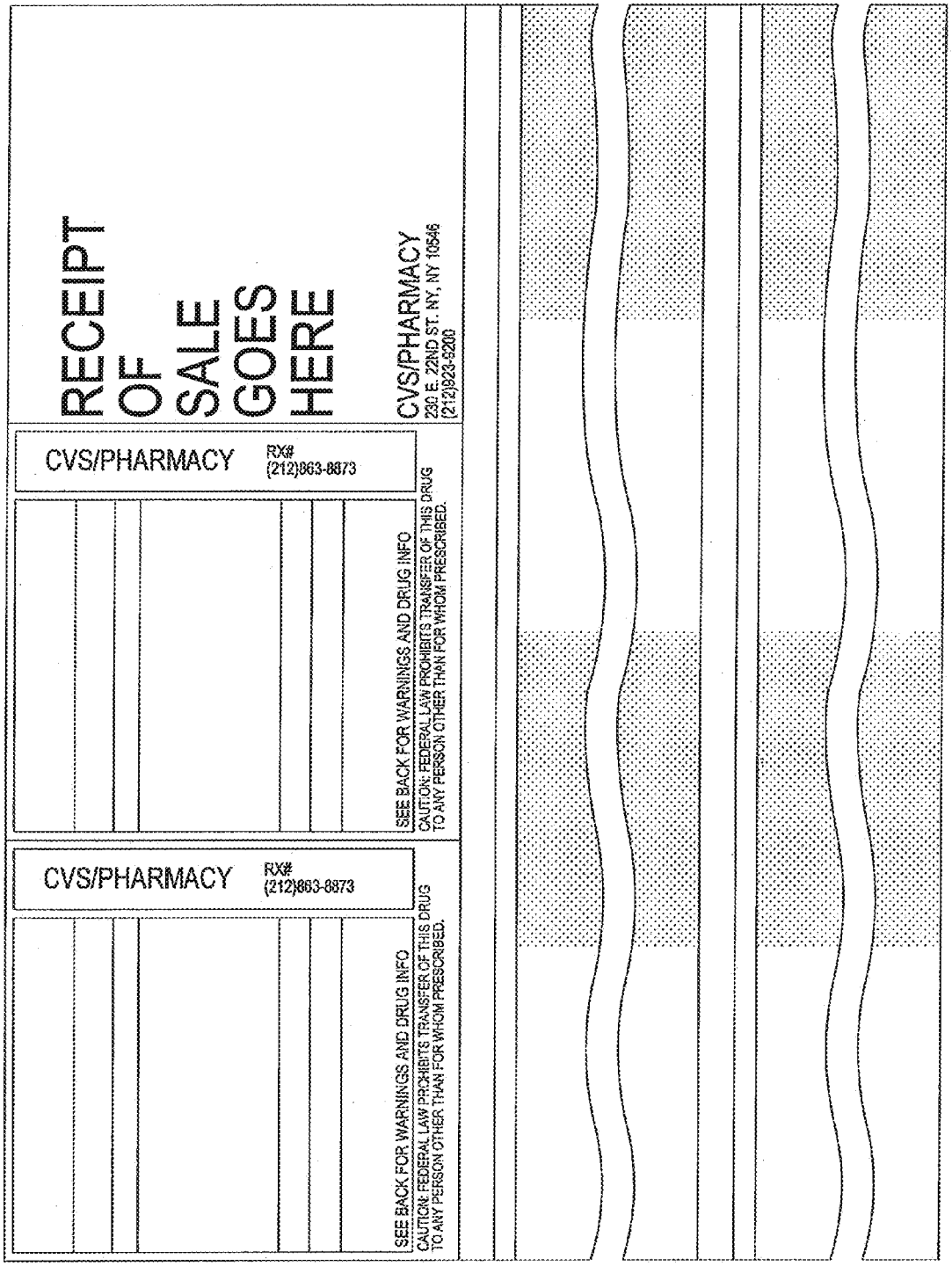
FIG. 10 shows a sheet having a label section and data section for creating labels in accordance with the invention.

In the practice of the invention, a label 10 is formed on a single sheet with the information regarding the medication. Such a sheet is shown in FIG. 10 wherein two labels 10 are provided along with two information areas and in FIG. 11 wherein the information about a particular prescription is printed.

While particular embodiments of the invention have been shown and described, it will be obvious to those skilled in the art that changes and modifications may be made without departing from the invention in its broader aspects. For example, the invention is not limited to prescription medications for humans but can also be applied to over-the-counter medications and medications for animals. Therefore, the aim in the appended claims is to cover all such changes and modifications as fall within the true spirit and scope of the invention.

I claim:

1. A prescription container assembly, comprising:
   a receptacle configured to receive medication and including:
   a front wall; and
   a rear planar wall forming a shoulder and including at least one medication warning identifier sticker applied to the rear planar wall;
   and wherein the shoulder of the rear planar wall defines a slot;
   a cover engaging the receptacle for sealing the receptacle;
   a label secured to the receptacle to form a labeled receptacle;
   a color identifier disposed on the labeled receptacle, the color identifier corresponding with at least one of a medication parameter and a patient parameter; and
   a medication information card containing information relating to the medication and being slidably and removably retained within the slot relative to the rear planar wall of the receptacle, and
   wherein the medication information card comprises a first portion including a prescription-related notation and wherein the medication information card and the slot are both sized and shaped so that upon full insertion of the medication information card within the slot, the first portion of the medication information card extends beyond an edge of the receptacle to make visible the prescription-related notation of the first portion of the medication information card beyond the edge of the receptacle, and wherein the at least one medication warning identifier sticker remains visible upon removal of the medication information card from the slot.

2. The prescription container assembly of claim 1 wherein the medication information card comprises a foldable member including a folded position configured to be slidably removably retained within the slot.

3. The prescription container assembly of claim 2, wherein the foldable member is configured to be repeatedly folded into and unfolded from the folded position.

4. The prescription container assembly of claim 1 and further comprising a magnifying lens, wherein the slot is sized and shaped to slidably removably retain both the magnifying lens and the medication information card.

5. The prescription container assembly of claim 1, in combination with medication contained in the receptacle.

6. The prescription container assembly of claim 1, wherein the prescription-related notation includes indicia located on the first portion of the medication information card, and the indicia is entirely legible beyond the edge of the receptacle.

7. The prescription container assembly of claim 6, wherein the edge of the receptacle is an outermost edge of the receptacle.

* * * * *